United States Patent [19]

Hartmann et al.

[11] 4,252,738
[45] Feb. 24, 1981

[54] 1,2-HALOHYDRINCARBOXYLIC ACID ESTERS AND A PROCESS FOR THEIR PREPARATION

[75] Inventors: Willy Hartmann; Hans-Georg Heine, both of Krefeld-Verdingen, Fed. Rep. of Germany

[73] Assignee: Bayer Aktiengesellschaft, Leverkusen, Fed. Rep. of Germany

[21] Appl. No.: 887,900

[22] Filed: Mar. 17, 1978

[30] Foreign Application Priority Data

Apr. 9, 1977 [DE] Fed. Rep. of Germany ....... 2715931

[51] Int. Cl.$^3$ .................... C07C 120/00; C07C 69/74; C07C 69/78; C07C 69/12
[52] U.S. Cl. ........................... 260/464; 260/340.5 R; 260/404; 260/408; 260/465 D; 568/435; 568/442; 568/425; 568/420; 560/1; 560/106; 560/123; 560/124; 560/125; 560/126; 560/127; 560/128; 560/129; 560/193; 560/240
[58] Field of Search ................. 260/465 D, 464, 463; 560/106, 240, 193, 1, 124, 123

[56] References Cited

U.S. PATENT DOCUMENTS

| | | | |
|---|---|---|---|
| 2,377,878 | 6/1945 | Gresham | 560/240 |
| 2,416,024 | 2/1947 | Senkus | 560/240 X |
| 2,607,800 | 8/1952 | Arundale | 560/240 |
| 3,062,852 | 11/1962 | Martin et al. | 560/106 X |
| 3,379,770 | 4/1968 | Elam et al. | 560/106 X |
| 3,410,892 | 11/1968 | Martin | 560/106 |
| 3,984,354 | 10/1976 | Schleppnik | 560/106 X |
| 4,110,539 | 8/1978 | Albers et al. | 560/240 |

FOREIGN PATENT DOCUMENTS

642489  9/1950  United Kingdom .................... 560/240

OTHER PUBLICATIONS

Hartman, Heine & Wendisch, Tetrahedron Letters, No. 26, Jun. 1977, pp. 2263–2266.

*Primary Examiner*—Joseph P. Brust
*Attorney, Agent, or Firm*—Sprung, Felfe, Horn, Lynch & Kramer

[57] ABSTRACT

1,2-Halohydrincarboxylic acid esters of the formula

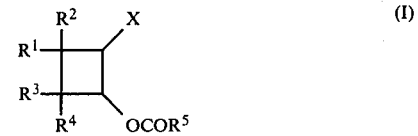

wherein
$R^1$, $R^2$, $R^3$, and $R^4$ are identical or different and represent hydrogen, cyano and optionally substituted alkyl, alkenyl, aralkyl, aryl, alkoxycarbonyl, acyloxy, alkoxy and aryloxy, and furthermore $R^1$ and $R^2$ and/or $R^3$ and $R^4$, or $R^1$ and $R^3$ and/or $R^2$ and $R^4$ can be linked, forming a ring with the carbon atoms to which they are bonded;
$R^5$ represents hydrogen and optionally substituted alkyl, alkenyl, aralkyl, aryl, alkoxy and alkoxycarbonyl and
X represents fluorine, chlorine, bromine and iodine; a process for preparing such 1,2-halohydrincarboxylic acid esters by reacting a cyclobutane-cis-1,2-diol of the formula

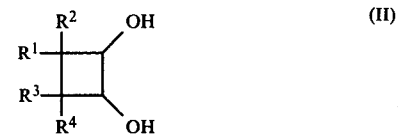

with an orthoester of the formula

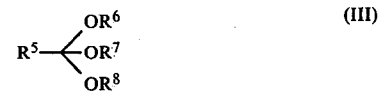

wherein $R^1$–$R^5$ have the previously ascribed significance and $R^6$–$R^8$ are identical or different and represent optionally substituted alkyl, alkenyl, aralkyl and aryl, (or a ketene-acetal corresponding thereto) to give a 1,3-dioxolane and reacting the resultant 1,3-dioxolane with a halogenosilane or an acid halide. Also disclosed is a process for preparing compounds of the formula

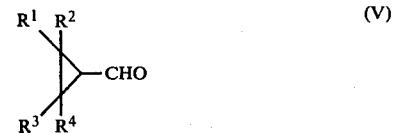

by contacting a 1,2-halohydrin ester of the formula given above with a base suitably at a temperature of 20° to 150° C.

9 Claims, No Drawings

1,2-HALOHYDRINCARBOXYLIC ACID ESTERS AND A PROCESS FOR THEIR PREPARATION

The present invention relates to new 1,2-halohydrincarboxylic acid esters of cyclobutane, a process for their preparation and their use for the preparation of cyclopropanecarbaldehydes.

Only one representative from the series of 1,2-halohydrincarboxylic acid esters of cyclobutanes has hitherto been described (Experientia 27, 1,378 (1971). This is 8-acetoxy-7-chloro-4,4,6-trimethyl-bicyclo[4,2,0]octan-2-one, which has been obtained by reacting the corresponding dichloride with zinc/glacial acetic acid. This route gives a poor yield and, because suitable starting compounds are not readily available, is not a useful process, and cannot be generally applied, for the synthesis of 1,2-halohydrin esters of the cyclobutane series. Furthermore, the reaction of 1,2-thiocarbonyldioxycyclobutanes with alkyl iodides to give alkylthiolcarbonates of the corresponding 1,2-iodohydrins is described in Tetrahedron Lett. 1973, 3,793 and J. Org. Chem. 39, 3,641 (1974), but this reaction is limited to the reaction with alkyl iodides.

According to the present invention there is provided a 1,2-Halohydrincarboxylic acid ester of the formula

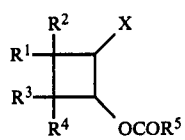

wherein
$R^1$, $R^2$, $R^3$ and $R^4$ are identical or different and represent hydrogen, cyano, optionally substituted alkyl, alkenyl, aralkyl, aryl, alkoxycarbonyl, acyloxy, alkoxy or aryloxy, and $R^1$ and $R^2$ and/or $R^3$ and $R^4$, or $R^1$ and $R^3$ and/or $R^2$ and $R^4$ can be linked, forming a ring with the carbon atoms to which they are bonded, $R^5$ represents hydrogen, optionally substituted alkyl, alkenyl, aralkyl, aryl, alkoxy or alkoxycarbonyl and X represents fluorine, chlorine, bromine or iodine.

The invention also provides a process for the preparation of a 1,2-halohydrincarboxylic acid ester of the general formula

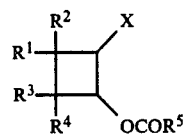

in which
$R^1$, $R^2$, $R^3$ $R^5$ and X have the above mentioned meanings wherein a cyclobutane-cis-1,2-diol of the general formula

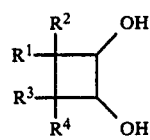

in which
$R^1$ to $R^4$ have the abovementioned meaning, is reacted with an orthoester of the general formula

wherein
$R^5$ has the meaning indicated above and
$R^6$, $R^7$ and $R^8$ are identical or different and represent optionally substituted alkyl, alkenyl, aralkyl or aryl or with a ketene-acetal which corresponds to the orthoester of the general formula (III) and which can be formally regarded as being formed by splitting off $R^6OH$, $R^7OH$ or $R^8OH$ from the compound of the general formula (III), to give a 1,3-dioxolane of the general formula

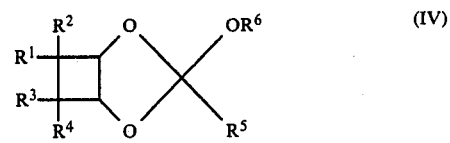

in which,
$R^1$ to $R^6$ have the meaning indicated above, and the compound of the general formula (IV) is then treated with a halogenosilane or acid halide, optionally in the presence of a catalyst and an inert organic solvent.

The process according to the invention can be represented by the general equation which follows: the reaction of cyclobutane-cis-1,2-diols with orthoesters to give the corresponding 1,3-dioxolanes, and the reaction thereof with halogenosilanes or acid halides to give the corresponding 1,2-halohydrincarboxylic acid esters.

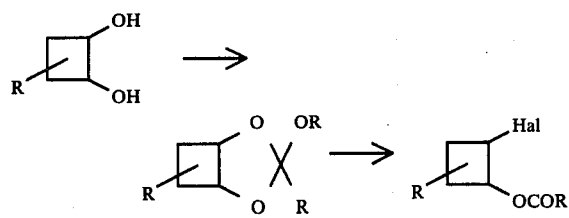

Examples of possible radicals $R^1$ to $R^6$ in the abovementioned formulae are hydrocarbon radicals with up to 12 C atoms, preferably up to 6 C atoms, for example alkyl radicals, such as methyl, ethyl, n-propyl, iso-propyl, tert.-butyl, n-butyl, iso-butyl, n-pentyl, n-octyl, n-decyl and n-dodecyl, preferably methyl and ethyl; furthermore, cycloalkyl radicals, such as cyclohexyl, cyclopropyl, cyclobutyl and cyclopentyl, preferably cyclohexyl; alkenyl radicals, such as vinyl, allyl and methallyl, preferably allyl; aralkyl radicals, such as benzyl, 4-chlorobenzyl and 3-phenylpropyl, preferably benzyl; aryl radicals, such as phenyl, tolyl and anisyl, preferably phenyl; alkoxycarbonyl radicals, such as methoxycarbonyl and ethoxycarbonyl, preferably ethoxycarbonyl; acyloxy radicals, such as acetoxy, benzoyloxy and trifluoroacetoxy, preferably acetoxy; alkoxy radicals, such as methoxy, ethoxy and tert.-butoxy, preferably methoxy; aryloxy radicals, such as phenoxy and p-tolyloxy, preferably phenoxy; and alkylene radicals, such as ethylene, trimethylene, tetramethylene and pentamethylene. $R^1$ and $R^6$ may also be styryl, phenoxycarbonyl, benzyloxy and an alkylene radical in which one or more methylene groups can optionally be replaced by heteroatoms such as 2-oxa-trimethylene and 1-thia-trimethylene.

Numerous cyclopropanecarbaldehydes of the general formula

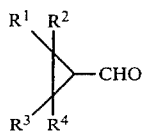

wherein
$R^1$ to $R^4$ have the meaning indicated for the compounds of the general formula (I),
can be obtained from the halohydrin esters of the general formula (I) by reaction with aqueous bases.

In order to prepare compounds of the general formula (I), one can, for example, react, in the first stage, one mol of a cyclobutane-cis-1,2-diol of the general formula (II), optionally in the presence of an inert organic solvent, such as toluene, xylene or benzene, but in general without the addition of a solvent of this type, with at least one mol, preferably with 1.1 to 3 mols, of an orthoester of the general formula (III), optionally in the presence of an acid catalyst, at elevated temperature, for example in a temperature range from about 60° to 140° C., preferably at 80° to 120° C., and to continuously distil off the alcohol liberated.

One can boil the mixture under reflux until the reaction has ended, and only then strip off the alcohol liberated.

Preferred cyclobutane-cis-1,2-diols are compounds of the formula

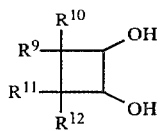

wherein,
$R^9$, $R^{10}$, $R^{11}$ and $R^{12}$ are identical or different and represent hydrogen, cyano, methyl, ethyl, n-propyl, isopropyl, n-butyl, iso-butyl, tert.-butyl, n-pentyl, n-decyl, cyclopropyl, cyclobutyl, cyclopentyl, cyclohexyl, vinyl, allyl, methallyl, styryl, benzyl, 4-chlorobenzyl, 3-phenylpropyl, phenyl, anisyl, methoxycarbonyl, ethoxycarbonyl, phenoxycarbonyl, acetoxy, benzoyloxy, trifluoroacetoxy, methoxy, ethoxy, tert.-butoxy, benzyloxy, phenoxy, p-tolyloxy, trimethylene, tetramethylene, pentamethylene, 2-oxa-trimethylene, or 1-thia-trimethylene.

The following cyclobutane-cis-1,2-diols may be mentioned as examples: cyclobutane-cis-1,2-diol, 3-methyl-cyclobutane-1,2-cis-diol, 3-ethyl-cyclobutane-cis-1,2-diol, 3-isopropyl-cyclobutane-cis-1,2-diol, 3-tert.-butyl-cyclobutane-cis-1,2-diol, 3,3-dimethyl-cyclobutane-cis-1,2-diol, 3,3,4,4-tetramethyl-cyclobutane-cis-1,2-diol, 3,3,4-trimethylcyclobutane-cis-1,2-diol, 3-methoxy-cyclobutane-cis-1,2-diol, 3-ethoxy-cyclobutane-cis-1,2-diol, 3-cyano-cyclobutane-cis-1,2-diol, 3,3-dimethyl-4-cyano-cyclobutane-cis-1,2-diol, 3,3-dimethyl-4-ethoxycarbonyl-cyclobutane-cis-1,2-diol, 3-vinyl-cyclobutane-cis-1,2-diol, 3-phenyl-cyclobutane-cis-1,2-diol, 3-benzyl-cyclobutane-cis-1,2-diol, spirohexane-cis-4,5-diol, spiro[3,3]heptane-cis-5,6-diol, bicyclo[3,2,0]heptane-cis-6,7-diol, bicyclo[4,2,0]octane-cis-7,8-diol and 3-oxa-bicyclo[3,2,0]heptane-cis-6,7-diol.

Diols having this structure are readily accessible by catalytic hydrogenation of the 1,2-bis-(trialkylsiloxy)cyclobut-1-enes (DT-OS (German Published Specification) No. 2,163,394) or by photosensitised cycloaddition of vinylene carbonate onto olefins (DT-OS (German Published Specification) No. 1,543,626) and subsequent hydrolysis.

The following compounds are examples of orthoesters of the general formula (III) which can be used: trimethoxymethane, triethoxymethane, tri-n-propoxymethane, 1,1,1-trimethoxyethane, 1,1,1-triethoxyethane, 1,1,1-tri-n-butoxyethane, 1,1,1-triethoxypropane, 1,1,1-trimethoxypropane, 1,1,1-triethoxybutane, 1,1,1-triethoxypentane, 1,1,1,-tri-n-propoxypentane, 1,1,1-trimethoxypentane, 1-cyclohexyl-1,1,1-trimethoxymethane, 2-phenyl-1,1,1-triethoxyethane, 2-phenyl-1,1,1-trimethoxyethane, 3-methyl-1,1,1-triethoxybutane, 1,1,1-trioctyloxyethane, 2-methyl-1,1,1-trimethoxypropane, 2-methyl-1,1,1-triethoxypropane, 1,1,1-tri-n-butoxypropane, 1,1,1-triethoxyacetic acid ethyl ester, 1-phenyl-1,1,1-trimethoxymethane and 1-phenyl-1,1,1-triethoxymethane.

In principle, all transesterification catalysts, such as are described, for example, in Houben-Weyl, Methoden der Organischen Chemie (Methods of Organic Chemistry), VIII, page 517 et seq., are suitable for catalysing the reaction of the compound of the formula (II) and (III).

Examples of acid catalysts which can be used are lower fatty acids, such as acetic acid, propionic acid, butyric acid, isobutyric acid, cyclohexylcarboxylic acid, malonic acid, succinic acid or adipic acid; aromatic carboxylic acids, such as benzoic acid, toluic acid or m-chlorobenzoic acid; sulphonic acids, such as benzenesulphonic acid or p-toluenesulphonic acid; mineral acids, such as hydrochloric acid, sulphuric acid, phosphoric acid or perchloric acid, and Lewis acids, such as aluminum chloride, zinc chloride, titanium tetrachloride, tin tetrachloride or boron trifluoride. As a rule, the catalysts are employed in amounts of about 0.01 to 10% by weight, preferably of 0.1 to 5% by weight, relative to the diol of the formula (II) employed.

According to a possible variant of the process for the preparation of compounds of the formula (I), the diol of the formula (II) is suspended, for example, in an orthoester of the formula (III), in general an acid catalyst, preferably benzoic acid and/or isobutyric acid, is added and the mixture is heated slowly until alcohol formed from the transesterification is distilled off, if necessary over a column. The reaction has ended when no further alcohol distils off. The reaction time is about 1 to about 10 hours, depending on the starting materials used. After complete conversion, the reaction mixture can be worked up by known processes in order to separate off excess orthoester and, if appropriate, catalysts. Thus, for example, the reaction mixture can be subjected to fractional distillation. However, one can also purify the reaction mixture by recrystallisation, especially if crystalline reaction products have been formed. Finally, the acid used as a catalyst can be removed from the crude reaction mixture by extraction with a base, such as aqueous sodium bicarbonate solution.

In the second reaction stage one can, for example, react 1 mol of a compound of the general formula (IV), optionally in the presence of an inert organic solvent, such as toluene, benzene, methylene chloride, carbon tetrachloride or 1,2-dichloroethane, but in general without the addition of a solvent of this type, with at least one molar equivalent, preferably with 1.1 to 1.5 molar equivalents, of a halogenosilane or an acid halide, optionally in the presence of a catalyst, at optionally elevated temperature and, after the reaction has ended, to distil or crystallise the product, optionally under reduced pressure. The new compounds of the general formula (I) according to the invention are always obtained here as trans-1,2-halohydrincarboxylic acid esters.

The following compounds are examples of halogenosilanes which can be used: trimethylchlorosilane, dichlorodimethylsilane, trimethyliodosilane, triphenylchlorosilane, triethylchlorosilane, trimethylbromosilane, trimethylfluorosilane, trichloromethylsilane, tetrachlorosilane and tetrafluorosilane; trimethylhalogenosilanes are preferably employed, such as trimethylchlorosilane, trimethylbromosilane and trimethyliodosilane.

Examples of acid halides which can be used are: halides of aliphatic or cycloaliphatic carboxylic acids, such as acetyl chloride, acetyl bromide, acetyl iodide, propionyl bromide, hexahydrobenzoyl chloride, phenylacetyl chloride and n-butyryl fluoride; and halides of aromatic carboxylic acids, such as benzoyl chloride, naphthoyl chloride and benzoyl bromide.

One can also use halides of aromatic and aliphatic sulphonic acids, such as methanesulphonyl chloride and benzenesulphonyl chloride, as well as halides of phosphonic acids, such as methanephosphonic acid chloride, furthermore thionyl chloride or sulphuryl chloride and phosphorus trihalides, such as phosphorus trichloride.

Lewis acids, for example aluminum trichloride, iron trichloride, zinc chloride, tin tetrachloride, boron fluoride-etherate and titanium tetrachloride, can be used as catalysts. In general, the amount of catalyst added is 0.1 to 5% by weight, preferably 0.1 to 2% by weight, relative to the orthoester of the general formula (IV) employed.

The conversions of the 1,3-dioxolanes of the general formula (IV) into compounds of the general formula (I) can be carried out in a temperature range from about 0° to 100° C., preferably 40° to 80° C.

Preferred 1,2-halohydrincarboxylic acid esters according to the invention are compounds of the formula

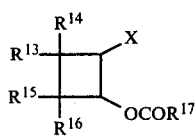

(VII)

wherein $R^{13}$, $R^{14}$, $R^{15}$ and $R^{16}$ are identical or different and represent hydrogen, cyano, methyl, ethyl, n-propyl, n-butyl, iso-propyl, iso-butyl, tert.-butyl, n-octyl, n-dodecyl, vinyl, allyl, methallyl, styryl, benzyl, 4-chlorobenzyl, 3-phenylpropyl, phenyl, tolyl, anisyl, methoxycarbonyl, ethoxycarbonyl, phenoxycarbonyl, acetoxybenzoyloxy, trifluoroacetoxy, methoxy, ethoxy, tert.-butoxy, benzyloxy, phenoxy, 4-tolyloxy, dimethylene, trimethylene, tetramethylene or pentamethylene, and $R^{17}$ denotes hydrogen, methyl, ethyl, n-propyl, iso-propyl, n-butyl, iso-butyl, tert.-butyl or phenyl and X represents fluorine, chlorine, bromine or iodine.

Particularly preferred new 1,2-halohydrincarboxylic acid esters are compounds of the formula

(VIII)

wherein $R^{18}$, $R^{19}$, $R^{20}$ and $R^{21}$ are identical or different and represent hydrogen, cyano, methyl, ethyl, iso-propyl, tert.-butyl, methoxycarbonyl, ethoxycarbonyl, benzyloxy, ethylene, trimethylene or tetramethylene, and $R^{22}$ denotes hydrogen, methyl, ethyl or phenyl and X represents fluorine, chlorine, bromine or iodine.

The following 1,2-halohydrincarboxylic acid esters of cyclobutane may be mentioned as examples: 1-chloro,2-acetoxycyclobutane, 1-bromo-2-acetoxycyclobutane, 1-iodo-2-acetoxycyclobutane, 1-chloro-2-benzoyloxy-cyclobutane, 1-bromo-2-benzoyloxycyclobutane, 1-iodo-2-acetoxy-3,3-dimethyl-cyclobutane, 1-chloro-2-acetoxy-3,3-dimethyl-cyclobutane, 1-bromo-2-acetoxy-3,3-dimethyl-cyclobutane, 1-chloro-2-acetoxy-3-tert.-butyl-cyclobutane, 4-chloro-5-acetoxy-spirohexane, 4-bromo-5-acetoxy-spirohexane, 7-chloro-8-acetoxy-bicyclo[4,2,0]octane and 1-chloro-4-methoxy-2-acetoxy-cyclobutane.

The process according to the invention is distinguished by its simplicity, its general applicability and also by the possibility of carrying it out on an industrial scale.

The 1,2-halohydrincarboxylic acid esters which can be prepared by the process according to the invention are interesting synthesis units for numerous compounds of the cyclobutane and cyclopropane series.

Thus, numerous novel cyclobutylcarboxylic acid esters are easily accessible, for example by dehalogenation, and, after hydrolysis to give the corresponding cyclobutanols, can be oxidised (compare, for example, J. Am. Chem. Soc. 96, 4,885 (1974)). This reaction sequence is variable and makes it possible to prepare cyclic ketones with a 4-membered ring, which are otherwise only obtainable with difficulty.

Cyclopropanecarbaldehydes of the general formula (V) can be smoothly obtained from compounds of the general formula (I) by the action of aqueous bases (2 N to 3 N) or of dilute acids (2 N to 3 N), such as sodium hydroxide solution or sulphuric acid. These aldehydes are intermediate products for the synthesis of, for example, insecticides (DT-OS (German Published Specification) No. 2,231,312).

For example, the carbaldehydes of the formula (V) can be easily oxidised to the corresponding carboxylic acids (atmospheric oxidation), which can be converted, according to DT-OS (German Published Specification) No. 2,231,312, into esters useful as insecticides.

A typical example is 2.2.3.3-tetramethylcyclopropanecarbaldehyde which can be oxidised according to known procedures (J. Org. Chem. 38, 4106 (1973)) to the corresponding acid. This acid can be easily converted into esters, for example into the m-phenoxy-2-cyanbenzyl ester. The use of the compound as an insecticide is disclosed in the above mentioned DT-OS 22 31 312.

In order to prepare the cyclopropanecarbaldehydes of the general formula (V), the procedure followed is to react the new 1,2-halohydrin ester of the general formula (I), obtainable from the reaction sequence 1,2-diol→1,3-dioxolane→1,2-halohydrin ester, at temperatures in the range from about 20° to 150° C., preferably 20° to 60° C., with a base, optionally in an inert, organic solvent.

Examples of suitable bases are sodium hydroxide solution, potassium hydroxide solution, sodium carbonate solution, alcoholic alkali metal hydroxide solution and solutions of alkali metal alcoholates in alcohols. Alkali metal hydroxide solutions, such as sodium hydroxide solution, are preferably used. In general, the bases are added in amounts of about 1 to 5 molar equivalents, preferably 3 molar equivalents, relative to mols of halohydrin ester of the general formula (I) employed. Examples of suitable inert organic solvents are: toluene, n-hexane, dimethoxyethane, dibutyl ether, methylene chloride, tetrahydrofurane and ethanol.

Ethanol is preferably used as the solvent.

The process according to the invention may be illustrated with the aid of the following Examples, but without it being limited to these Examples.

EXAMPLE 1

130.8 g (1.5 mols) of cyclobutane-cis-1,2-diol, 222.6 g (1.5 mols) of orthoformic acid ethyl ester and 15.0 g of benzoic acid are heated from 90° to 120° C. in the course of 3 hours. The ethanol which forms is distilled off continuously. Fractional distillation in vacuo gives 179.5 g (83%) of 3-ethoxy-2,4-dioxa-bicyclo[3,2,0]heptane (stereoisomer mixture), boiling point$_{11}$ 63°.

$C_7H_{12}O_3$ (114.2) calculated: C 58.32, H 8.39, O 33.29; found: C 58.1, H 8.11, O 33.2.

EXAMPLE 2

21.5 g (0.25 mol) of cyclobutane-cis-1,2-diol, 47.8 g (0.26 mol) of orthobenzoic acid trimethyl ester and 0.5 g of benzoic acid are heated to 100° to 150° C. in the course of 3 hours. The methanol which forms is distilled off continuously. The residue is subjected to fractional distillation and gives 40.0 g (78%) of 3-methoxy-3-phenyl-2,4-dioxa-bicyclo[3,2,0]heptane (stereoisomer mixture) of boiling point$_{0.7}$ 92°.

$C_{12}H_{14}O_3$ (206.2) calculated: C 69.88, H 6.84, O 23.27; found: C 69.8, H 6.94, O 23.3.

EXAMPLE 3

88.0 g (1.0 mol) of cyclobutane-cis-1,2-diol, 120.0 g (1.0 mol) of orthoacetic acid methyl ester and 10.0 g of benzoic acid are heated from 80° to 120° C. in the course of 3 hours. Methanol which forms is distilled off continuously. Fractional distillation gives 114.0 g (79%) of 3-methoxy-3-methyl-2,4-dioxa-bicyclo[3,2,0]heptane (stereoisomer mixture) of boiling point$_{12}$ 52°–53°.

$C_7H_{12}O_3$ (144.2) calculated: C 58.32, H 8.39, O 33.29; found: C 58.0, H 8.50, O 33.4.

EXAMPLE 4

14.4 g (0.1 mol) of trans-3-tert.-butyl-cyclobutane-cis-1,2-diol, 13.2 g (0.11 mol) of orthoacetic acid methyl ester and 0.2 g of benzoic acid are reacted as described in Example 3. 17.0 g (85%) of 3-methoxy-3-methyl-6-exo-tert.-butyl-2,4-dioxa-bicyclo[3,2,0]heptane (stereoisomer mixture), boiling point$_{13}$ 72°–73°.

$C_{11}H_{20}O_3$ (200.3) calculated: C 65.97, H 10.07, O 23.97; found: C 65.6, H 10.0, O 23.7.

EXAMPLE 5

41.6 g (0.353 mol) of cis-3-methoxy-cyclobutane-cis-1,2-diol, 42.3 g (0.352 mol) of orthoacetic acid methyl ester and 1.5 g of benzoic acid are heated to 120° C. until the calculated amount of methanol has distilled off. Customary working up gives 51.0 g (83%) of 3-methoxy-3-methyl-6-endo-methoxy-2,4-dioxa-bicyclo[3,2,0]heptane (stereoisomer mixture) of boiling point$_{12}$ 85°–90°, $C_8H_{14}O_4$ (174.2) calculated: C 55.16, H 8.10, O 36.74; found: C 54.9, H 8.2, O 36.5.

EXAMPLE 6

205.0 g (1.77 mols) of 3,3-dimethyl-cyclobutane-cis-1,2-diol, 233.0 g (1.94 mols) of orthoacetic acid methyl ester and 2.0 g of p-toluenesulphonic acid are heated from 90° to 120° C. in the course of 3 hours. Distilling off the methanol which forms and subsequent fractionation gives 281.0 g (93%) of 3-methoxy-3,6,6-trimethyl-2,4-dioxo-bicyclo[3,2,0]heptane as a mixture of two stereoisomers, boiling point$_{16}$ 74°–76°.

$C_9H_{16}O_3$ (172.2) calculated: C 62.77, H 9.56, O 27.88; found: C 62.5, H 9.2, O 27.5.

EXAMPLE 7

48.0 g (0.334 mol) of 3,3,4,4-tetramethyl-cyclobutane-cis-1,2-diol, 44.0 g (0.366 mol) of orthoacetic acid methyl ester and 0.4 g of benzoic acid are heated from 100° to 120° C. in the course of 4 hours. Methanol which forms is distilled off continuously. Fractional distillation gives 50.1 g (75%) of 3-methoxy-3,6,6,7,7-pentamethyl-2,4-dioxa-bicyclo[3,2,0]heptane as a stereoisomer mixture of boiling point$_{13}$ 93°–96°.

$C_{11}H_{20}O_3$ (200.3) calculated: C 65.97, H 10.07, O 23.97; found: C 65.6, H 9.9, O 23.6.

EXAMPLE 8

39.0 g (0.34 mol) of spirohexane-cis-4,5-diol, 44.0 g (0.367 mol) of orthoacetic acid methyl ester and 0.5 g of benzoic acid are heated in a manner such that the methanol which forms distils off slowly. After 3 hours, the solution is subjected to fractional distillation. This gives 52.9 g (92%) of 3'-methoxy-3'-methyl-spiro[cyclopropane-1,6'-dioxa-(2',4')-bicyclo[3,2,0]heptane] as a mixture of two stereoisomers. Boiling point$_{11}$ 78°–82°.

$C_9H_{14}O_3$ (170.2) calculated: C 63.51, H 8.29, O 28.20; found: C 63.3, H 8.3, O 28.0.

EXAMPLE 9

219.0 g (1.54 mols) of bicyclo[4,2,0]octane-endo-cis-7,8-diol, 204.0 g (1.7 mols) of orthoacetic acid methyl ester and 10.0 g of benzoic acid are heated from 100° to 120° C. in the course of 3 hours. The methanol which is formed is distilled off continuously. Fractional distillation in vacuo gives 290.0 g (95%) of 10-methoxy-10-methyl-9,11-dioxa-endo-tricyclo[6,3,0,0$^{2,7}$]undecane as a mixture of two stereoisomers. Boiling point$_{0.1}$ 62.5°–63.5°.

$C_{11}H_{18}O_3$ (198.3) calculated: C 66.64, H 9.15, O 24.21; found: C 66.4, H 9.07, O 24.6.

EXAMPLE 10

14.4 g (0.1 mol) of 3-methoxy-3-methyl-2,4-dioxa-bicyclo[3,2,0]heptane (stereoisomer mixture) and 16.2 g (0.149 mol) of trimethylchlorosilane in 50 ml of methylene chloride are heated under reflux for 15 hours. Stripping off the solvent and fractional distillation of the residue gives 13.2 g (89%) of trans-1-chloro-2-acetoxy-cyclobutane. Boiling point$_{10}$ 66°, n$_D^{20}$ 1.4472.

$C_6H_9ClO_2$ (148.6) calculated: C 48.50, H 6.11, Cl 23.86, O 21.54; found: C 48.40, H 6.21, Cl 23.00, O 21.00.

EXAMPLE 11

107.0 g (0.743 mol) of 3-methoxy-3-methyl-2,4-dioxa-bicyclo[3,2,0]heptane (stereoisomer mixture) and 122.0 g (0.8 mol) of trimethylbromosilane are heated under reflux in 400 ml of methylene chloride for 15 hours. Concentration and distillation in vacuo give 132.9 g (93%) of trans-1-bromo-2-acetoxy-cyclobutane. Boiling point$_{11}$ 78°, n$_D^{20}$ 1.4748.

$C_6H_9BrO_2$ (193.0) calculated: C 37.33, H 4.70, Br 41.39, O 16.58; found: C 37.4, H 4.8, Br 40.9, O 16.2.

EXAMPLE 12

73.4 g (0.51 mol) of 3-methoxy-3-methyl-2,4-dioxa-bicyclo[3,2,0]heptane (stereoisomer mixture) and 102.0 g (0.51 mol) of trimethyliodosilane in 300 ml of methylene chloride are heated to the reflux for 15 hours. Working up by distillation gives 93.6 g (82%) of trans-1-iodo-2-acetoxy-cyclobutane. Boiling point$_{12}$ 94°–95°, n$_D^{20}$ 1.5203.

$C_6H_9IO_2$ (240.1) calculated: C 30.02, H 3.78, I 52.87, O 13.33; found: C 30.0, H 3.7, I 53.0, O 13.6.

EXAMPLE 13

28.9 g (0.2 mol) of 3-methoxy-3-methyl-2,4-dioxa-bicyclo[3,2,0]heptane (stereoisomer mixture) and 15.4 g (0.2 mol) of acetyl chloride are heated to the reflux for 5 hours. Distillation in vacuo gives 24.8 g (84%) of trans-1-chloro-2-acetoxy-cyclobutane. Boiling point$_{19}$ 79°, n$_D^{20}$ 1.4473.

EXAMPLE 14

A mixture, as described in Example 13, but with 26.8 g (0.3 mol) of acetyl bromide, gives, after customary working up, 35.8 g (93%) of trans-1-bromo-2-acetoxy-cyclobutane. Boiling point$_{13}$ 87°, n$_D^{20}$ 1.4735.

EXAMPLE 15

26.0 g (0.126 mol) of 3-methoxy-3-phenyl-2,4-dioxa-bicyclo[3,2,0]heptane (stereoisomer mixture) and 17.1 g (0.16 mol) of trimethylchlorosilane in 70 ml of methylene chloride are heated to the reflux for 14 hours. Evaporation and fractional distillation in vacuo gives 25.9 g (98%) of trans-1-chloro-2-benzoyloxy-cyclobutane. Boiling point$_{0.35}$ 94°–95°, melting point 20°.

$C_{11}H_{11}ClO_2$ (210.7) calculated: C 62.72, H 5.26, Cl 16.83, O 15.19; found: C 62.5, H 5.1, Cl 16.7, O 15.2.

EXAMPLE 16

16.9 g (0.189 mol) of acetyl bromide are added dropwise to 26.0 g (0.126 mol) of 3-methoxy-3-phenyl-2,4-dioxa-bicyclo[3,2,0]heptane (stereoisomer mixture), at 20° to 30° C. After the reaction has subsided, the mixture is heated to the reflux for 4 hours. Distillation in vacuo gives 32.5 g (99%) of trans-1-bromo-2-benzoyloxy-cyclobutane as a colourless oil of boiling point$_{0.2}$ 94°–97°, which solidifies in the receiver.

Melting point 38°–40° (from petroleum ether).

$C_{11}H_{11}BrO_2$ (255.1) calculated: C 51.79, H 4.35, Br 31.32, O 12.54; found: C 51.8, H 4.2, Br 31.3, O 12.7.

EXAMPLE 17

267.0 g (1.55 mols) of 3-methoxy-3,6,6-trimethyl-2,4-dioxa-bicyclo[3,2,0]heptane and 185.0 g (1.7 mols) of trimethylchlorosilane in 700 ml of methylene chloride are reacted as described for Example 10. 243.5 g (89%) of trans-1-chloro-2-acetoxy-3,3-dimethyl-cyclobutane. Boiling point$_{0.4}$ 30°, n$_D^{20}$ 1.4410.

$C_8H_{13}ClO_2$ (176.6) calculated: C 54.50, H 7.42, Cl 20.07, O 18.11; found: C 54.4, H 7.3, Cl 19.9, O 18.4.

EXAMPLE 18

34.4 g (0.2 mol) of 3-methoxy-3,6,6-trimethyl-2,4-dioxa-bicyclo[3,2,0]heptane (stereoisomer mixture) and 33.6 g (0.22 mol) of trimethylbromosilane in 150 ml of methylene chloride are heated to the reflux for 15 hours. Evaporation and fractional distillation of the residue in vacuo give 34.9 g (79%) of trans-1-bromo-2-acetoxy-3,3-dimethyl-cyclobutane. Boiling point$_{14}$ 87°–89°, n$_D^{20}$ 1.4629.

$C_8H_{13}BrO_2$ (221.1) calculated: C 43.46, H 5.93, Br 36.14, O 14.47; found: C 43.6, H 5.9, Br 36.1, O 14.8.

EXAMPLE 19

34.4 g (0.2 mol) of 3-methoxy-3,6,6-trimethyl-2,4-dioxa-bicyclo[3,2,0]heptane (stereoisomer mixture) and 44.0 g (0.22 mol) of trimethyliodosilane are heated to the reflux in 150 ml of methylene chloride for 15 hours. Concentration and fractional distillation in vacuo give 40.2 g (75%) of trans-1-iodo-2-acetoxy-3,3-dimethyl-cyclobutane. Boiling point$_{0.1}$ 38°–39°, n$_D^{20}$ 1.5008.

$C_8H_{13}IO_2$ (268.1) calculated: C 35.84, H 4.89, I 47.34, O 11.94; found: C 35.5, H 4.7, I 47.0, O 11.6.

EXAMPLE 20

50.7 g (0.3 mol) of 3'-methoxy-3'-methyl-spiro[cyclopropane-1,6'-dioxa(2',4')-bicyclo[3,2,0]heptane] (stereoisomer mixture) and 35.8 g (0.33 mol) of trimethylchlorosilane in 150 ml of methylene chloride are heated to the reflux for 15 hours. Distillation in vacuo gives 57.2 g (98%) of trans-4-chloro-5-acetoxy-spirohexane. Boiling point$_{13}$ 88°–90°, n$_D^{20}$ 1.4625.

$C_8H_{11}ClO_2$ (174.6) calculated: C 55.02, H 6.35, Cl 20.30, O 18.32; found: C 54.8, H 6.2, Cl 19.9, O 18.1.

EXAMPLE 21

12.8 g (0.075 mol) of 3'-methoxy-3'-methyl-spiro[cyclopropane-1,6'-dioxa-(2',4')-bicyclo[3,2,0]heptane] (stereoisomer mixture) and 12.6 g (0.083 mol) of trimethylbromosilane in 75 ml of methylene chloride are heated to the reflux for 18 hours. Fractional distillation in vacuo gives 15.4 g (94%) of trans-4-bromo-5-acetoxy-spirohexane. Boiling point$_{0.3}$ 46°, n$_D^{20}$ 1.4872.

$C_8H_{11}BrO_2$ (219.1) calculated: C 43.86, H 5.06, Br 36.48, O 14.61; found: C 43.8, H 4.9, Br 36.2, O 14.8.

EXAMPLE 22

64.5 g (0.323 mol) of 3-methoxy-3-methyl-6-exo-tert.-butyl-2,4-dioxa-bicyclo[3,2,0]heptane stereoisomer mixture and 39.0 g (0.36 mol) of trimethylchlorosilane in 150 ml of methylene chloride are heated to the reflux for 15 hours. Concentration and distillation in vacuo give 59.5 g (90%) of trans-2-chloro-trans-4-tert.-butyl-1-acetoxy-cyclobutane. Boiling point$_{12}$ 101°–103° C., n$_D^{20}$ 1.4448.

$C_{10}H_{17}ClO_2$ (204.7) calculated: C 58.68, H 8.37, Cl 17.32, O 15.63; found: C 58.6, H 8.1, Cl 17.0, O 15.2.

EXAMPLE 23

245.0 g (1.24 mols) of 10-methoxy-10-methyl-endo-9,11-dioxa-tricyclo[6,3,0,0$^{2,7}$]undecane (stereoisomer mixture) and 148.0 g (1.36 mols) of trimethylchlorosilane in 500 ml of methylene chloride are heated to the reflux for 15 hours. Stripping off the solvent and fractional distillation of the residue in vacuo give 217.0 g (87%) of trans-7-chloro-8-cis-acetoxy-cis-bicyclo[4,2,0]octane. Boiling point$_{0.3}$ 78°, $n_D^{20}$ 1.4732.

$C_{10}H_{15}ClO_2$ (202.7) calculated: C 59.25, H 7.46, Cl 17.50, O 15.79; found: C 59.0, H 7.5, Cl 17.6, O 15.5.

EXAMPLE 24

42.6 g (0.245 mol) of 3-methoxy-3-methyl-endo-6-methoxy-2,4-dioxa-bicyclo[3,2,0]heptane (stereoisomer mixture) and 29.3 g (0.27 mol) of trimethylchlorosilane in 120 ml of methylene chloride are heated to the reflux for 15 hours. Concentration and fractional distillation in vacuo give 41.6 g (95%) of a 40:60 mixture of trans-1-chloro-cis-3-methoxy- and trans-1-chloro-cis-4-methoxy-2-acetoxy-cyclobutane. Boiling point$_{12}$ 93°–100°.

$C_7H_{11}ClO_3$ (178.6) calculated: C 47.07, H 6.21, Cl 19.85, O 26.87; found: C 46.8, H 6.2, Cl 19.5, O 27.0.

EXAMPLE 25

402.2 g (2.72 mols) of trans-1-chloro-2-acetoxy-cyclobutane and 2,720 ml of 3 N NaOH are stirred at 25° C. for 20 hours under nitrogen. The solution is then exhaustively extracted with ether in a Kutscher-Steudel apparatus. Drying the ether phase over sodium sulphate, distilling off the ether over a 40 cm Vigreux column and fractional distillation of the residue give 162.0 g (85%) of cyclopropanecarbaldehyde of boiling point 97°–99°.

EXAMPLE 26

48.9 g (0.28 mol) of trans-4-chloro-5-acetoxy-spirohexane and 280 ml of 3 N NaOH are stirred at 60° C. for 20 hours under nitrogen. Working up as described in the above Example gives 18.1 g (68%) of spiropentanecarbaldehyde. Boiling point 139.5°–140°, $n_D^{20}$ 1.4628.

$C_6H_8O$ (96.1) calculated: C 74.97, H 8.39, O 16.65; found: C 74.4, H 8.0, O 17.0.

EXAMPLE 27

67.2 g (0.328 mol) of trans-1-chloro-3-tert.-butyl-2-acetoxy-cyclobutane and 328 ml of 3 N NaOH are stirred at 20° C. for 20 hours under nitrogen. Thereafter, the mixture is extracted 3 times with 200 ml of ether each time and the combined ether phases are dried and give, after fractional distillation, 29.0 g (70%) of 2-tert.-butyl-cyclopropanecarbaldehyde (cis/trans mixture). Boiling point$_{14}$ 54°–56°. An analytically homogeneous sample can be obtained by distillation in a Fischer split tube column.

$C_8H_{14}O$ (126.2) calculated: C 76.14, H 11.18, O 12.68; found: C 75.8, H 10.8, O 13.0.

EXAMPLE 28

178.0 g (0.875 mol) of exo-7-chloro-endo-8-acetoxy-cis-bicyclo[4,2,0]octane are saponified with 875 ml of 3 N NaOH at 60° C. for 20 hours under nitrogen. Working up as described for Example 27 gives 81.1 g (75%) of exo-norcaranecarbaldehyde. Boiling point$_{15}$ 88°–90°, $n_D^{20}$ 1.4891.

EXAMPLE 29

222.0 g (1.26 mol) of tans-1-chloro-2-acetoxy-3,3-dimethyl-cyclobutane and 1.260 ml of 3 N NaOH are stirred at 60° C. for 20 hours under nitrogen. Thereafter, the reaction solution is extracted 8 times with 300 ml of ether each time. Evaporation of the ether phases, which have been dried over sodium sulphate, and distillation in vacuo give 91.8 g (74%) of 2,2-dimethyl-cyclopropanecarbaldehyde. Boiling point$_{11}$ 24°, $n_D^{20}$ 1.4332.

$C_6H_{10}O$ (98.1) calculated: C 73.43, H 10.27, O 16.30; found: C 72.9, H 9.7, O 16.6.

EXAMPLE 30

72.0 g (0.3 mol) of trans-1-iodo-2-acetoxy-cyclobutane in 150 ml of dry dioxane are catalytically (Pd/C) hydrogenated under normal pressure and at 20° C. in the presence of 33.2 g (0.33 mol) of dry triethylamine. The triethylammonium iodide formed is then filtered off and the filtrate is subjected to fractional distillation. This gives 25.2 g (74%) of cyclobutyl acetate (98% pure according to analysis by gas chromatography). Boiling point$_{760}$ 128°–129° $n_D^{20}$ 1.4175.

$C_6H_{10}O_2$ (114.1) calculated: C 63.13, H 8.83, O 28.03; found: C 63.3, H 8.7, O 28.0.

What is claimed is:

1. A process for the preparation of 1,2-halohydrincarboxylic acid esters of the formula

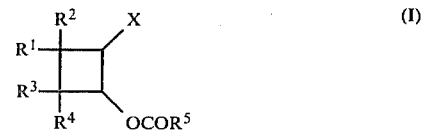

wherein $R^1$, $R^2$, $R^3$ and $R^4$ are identical or different and represent styryl, phenoxycarbonyl, benzyloxy, acetoxy, benzoyloxy, trifluoroacetoxy, hydrogen, alkyl, alkenyl, aralkyl, aryl, cyano, alkoxycarbonyl, alkoxy or aryloxy, and furthermore $R^1$ and $R^2$ and/or $R^3$ and $R^4$, or $R^1$ and $R^3$ and/or $R^2$ and $R^4$ can be linked, forming a bycyclo or spiro ring with the carbon atoms to which they are bonded, and $R^5$ is hydrogen, methyl, ethyl, n-propyl, n-butyl, cyclohexyl, benzyl, isobutyl, isopropyl, ethoxycarbonyl or phenyl and X represents fluorine, chlorine, bromine or iodine, which comprises contacting spirohexane-cis-4,5-diol, spiro[3,3]heptane-cis-5,6-diol, bicyclo[3,2,0]heptane-cis-6,7-diol, bicyclo[4,2,0]octane-cis-7,8-diol, 3-oxa-bicyclo[3,2,0]heptane-cis-6,7-diol or a cyclobutane-cis-1,2-diol of the formula

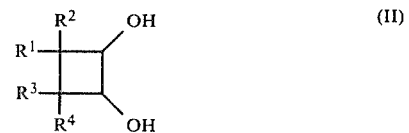

wherein $R^1$ to $R^4$ are identical or different and represent styryl, phenoxycarbonyl, benzyloxy, acetoxy, benzoyloxy, trifluoroacetoxy, hydrogen, alkyl, alkenyl, aralkyl, aryl, cyano, alkoxycarbonyl, alkoxy or aryloxy with an orthoester selected from the group consisting of trimethoxymethane, triethoxymethane, tri-n-propoxymethane, 1,1,1-trimethoxyethane, 1,1,1-triethoxyethane, 1,1,1-tri-n-butoxyethane, 1,1,1-tri-ethoxypropane, 1,1,1-trimethoxypropane, 1,1,1-triethoxybutane, 1,1,1-triethoxypentane, 1,1,1-tri-n-propoxypentane, 1,1,1-trimethoxypentane, 1-cyclo-hexyl-1,1,1-trimethoxymethane, 2-phenyl-1,1,1-triethoxyethane, 2-phenyl-1,1,1-trimethoxyethane, 3-methyl-1,1,1-triethoxybutane, 1,1,1-trioctyloxyethane, 2-methyl-1,1,1-trimethoxypropane, 2-methyl-1,1,1-triethoxypropane, 1,1,1-tri-n-butoxypropane, 1,1,1-triethoxyacetic acid ethyl ester, 1-phenyl-1,1,1-trimethoxymethane and 1-phenyl-1,1,1-triethoxymethane to give a 1,3-dioxolane of the formula

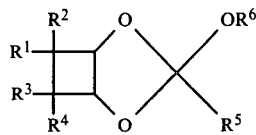

wherein
R¹ to R⁵ have the meaning indicated above,
R⁶ is alkyl,
and the radicals R¹ to R⁶ have up to 12 carbon atoms, at a temperature of 60° to 140° C. in the presence of an acid catalyst in an inert organic solvent employing said orthoester in an amount of 1.1 to 3 times the molar amount of said spirohexane-cis-4,5-diol, spiro[3,3]heptane-cis-5,6-diol, bicyclo[3,2,0]heptane-cis-6,7-diol, bicyclo[4,2,0]octane-cis-7,8-diol and 3-oxa-bicyclo[3,2,0]heptane-cis-6,7-diol or of said cyclobutane-cis-1,2-diol of said formula and thereafter contacting the resultant 1,3-dioxolane with a halogenosilane or an acid halide, selected from a group consisting of acetyl chloride, acetyl bromide, acetyl iodide, propionyl bromide, hexahydrobenzoyl chloride, phenylacetyl chloride, n-butyryl fluoride, benzoyl chloride, naphthoyl chloride, benzoyl bromide, methane sulphonyl chloride, benzene sulphonyl chloride, thionyl chloride phosgene, sulphuryl chloride or a phosphorus trihalide employing 1.1 to 1.5 molar equivalents of said halogenosilane, acid halide, thionyl chloride, phosgene, sulphuryl chloride or phosphorus trihalide per mol of 1,3-dioxolane in the presence of a Lewis acid which is employed in an amount of 0.1 to 5% by weight, based upon the amount of orthoester employed.

2. A process according to claim 1, wherein the process is carried out in toluene, xylene or benzene as the inert organic solvent.

3. A process according to claim 1, wherein said acid catalyst is a lower fatty acid, aromatic carboxylic acid, a sulphonic acid, a mineral acid and/or a Lewis acid.

4. A process according to claim 1, wherein said acid catalyst is benzoic acid and/or isobutyric acid.

5. A process according to claim 1, wherein the catalyst is employed in an amount of 0.01 to 10% by weight, based upon the amount of cyclobutane-diol employed.

6. A process according to claim 1, wherein a halogenosilane is employed which is a trimethylhalogenosilane.

7. A process according to claim 1, wherein the acid halide is acetyl chloride, acetyl bromide or phosgene.

8. A process according to claim 1, wherein the Lewis acid is zinc chloride, titanium tetrachloride or boron trifluoride.

9. A process according to claim 1, wherein the conversion of the 1,3-dioxolane into the corresponding 1,2-halohydrin ester is effected in the presence of toluene, benzene, methylene chloride, carbon tetrachloride or 1,2-dichloroethane.

* * * * *